(12) United States Patent
Sussan et al.

(10) Patent No.: US 8,158,161 B2
(45) Date of Patent: Apr. 17, 2012

(54) METHODS AND PHARMACEUTICAL COMPOSITIONS USEFUL FOR TREATING PSORIASIS

(75) Inventors: Ihab Sussan, Tarshiha (IL); Habib Sussan, Tarshiha (IL)

(73) Assignees: S.U.L.V.E. Ltd., Kfar Vradlm (IL); Gavish-Galilee Bio Applications Ltd., Kiryat-Shmona (IL)

( * ) Notice: Subject to any disclaimer, the term of this patent is extended or adjusted under 35 U.S.C. 154(b) by 503 days.

(21) Appl. No.: 11/794,926

(22) PCT Filed: Jan. 12, 2006

(86) PCT No.: PCT/IL2006/000055
§ 371 (c)(1),
(2), (4) Date: Jul. 9, 2007

(87) PCT Pub. No.: WO2006/075330
PCT Pub. Date: Jul. 20, 2006

(65) Prior Publication Data
US 2008/0044497 A1    Feb. 21, 2008

Related U.S. Application Data

(60) Provisional application No. 60/642,974, filed on Jan. 12, 2005.

(51) Int. Cl.
*A01N 65/00*    (2009.01)

(52) U.S. Cl. .................................................. 424/725
(58) Field of Classification Search .................. None
See application file for complete search history.

(56) References Cited

U.S. PATENT DOCUMENTS

| 5,952,373 A | 9/1999 | Lanzendörfer et al. |
| 2004/0258778 A1 * | 12/2004 | Farmar et al. ................. 424/755 |

FOREIGN PATENT DOCUMENTS

| WO | WO 03/063885 | * | 8/2003 |
| WO | WO 2006/075330 | | 7/2006 |

OTHER PUBLICATIONS

Office Action Dated May 2, 2010 From the Israel Patent Office Re.: Application No. 184547 and Its Translation Into English.
Examiner's Report Dated May 27, 2010 From the Australian Government, IP Australia Re. Application No. 2006205561.
Response Dated Oct. 3, 2010 to Office Action of May 2, 2010 From the Israel Patent Office Re.: Application No. 184547.
Verkerk et al. "Glucosinolates in Brassica Vegetables. The Influence of the Food Supply Chain on Intake, Bioavailability and Human Health", Molecular Nutrition and Food Research, 53: S219-S265, 2009.
International Preliminary Report on Patentability Dated Jul. 26, 2007 From the International Bureau of WIPO Re.: Application No. PCT/IL2006/000055.

\* cited by examiner

*Primary Examiner* — Michael Meller

(57) ABSTRACT

Pharmaceutical or cosmetic compositions including cruciferous plant extract or isothiocyanates such as 4-methyl-thio-butyl-isothiocyanate which are useful for treating psoriasis are provided.

2 Claims, 11 Drawing Sheets
(5 of 11 Drawing Sheet(s) Filed in Color)

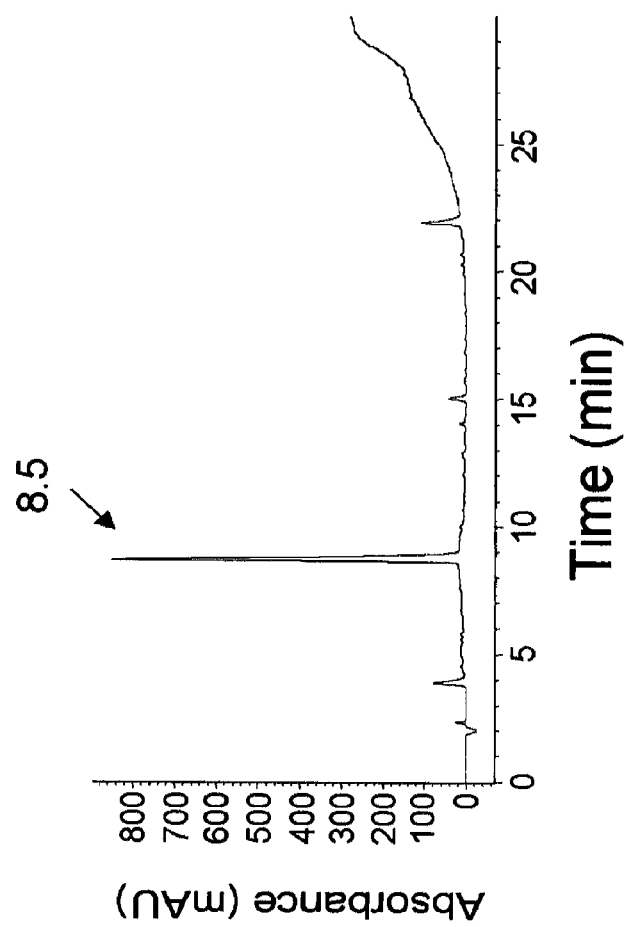

METHODS AND PHARMACEUTICAL COMPOSITIONS USEFUL FOR TREATING PSORIASIS

RELATED APPLICATIONS

This Application is a National Phase of PCT Patent Application No. PCT/IL2006/000055 having International Filing Date of Jan. 12, 2006, which claims the benefit of U.S. Provisional Patent Application No. 60/642,974 filed on Jan. 12, 2005. The contents of the above Applications are all incorporated herein by reference.

FIELD AND BACKGROUND OF THE INVENTION

The present invention relates to pharmaceutical compositions useful for treating psoriasis and, more particularly, to a cruciferous plant extract and/or isothiocyanates which are capable of treating psoriasis lesions.

Psoriasis is a common, non-contagious, chronic skin disease affecting 2-4% of the Caucasian population. The main characteristics of the disease include the appearance of thick red zones of the skin covered by silvery or whitish scaled eruptions and plaques of various sizes and which exhibit variable degrees of pruritus. The extent of the disease is variable, with small local areas or the whole surface of the body being affected. The disease may also affect the joints, nails and the mucous membranes. The precise cause of psoriasis is still unclear. While traumatized areas may often develop lesions of psoriasis, some external factors such as infections, stress, and medications (e.g. lithium, beta blockers, and anti-malarias) may exacerbate psoriasis. Scaling occurs when cells in the outer layer of skin (cutaneous cells) reproduce faster than normal and pile up on the skin's surface. Such high production of cutaneous cells is probably mediated by the immunological system.

The most common variety of psoriasis is called plaque type. Patients with plaque-type psoriasis exhibit stable, slowly growing plaques, which remain unchanged for long periods of time. The most common areas for plaque psoriasis to occur are the elbows knees, gluteal cleft, and the scalp. Involvement tends to be symmetrical.

Eruptive psoriasis (guttate psoriasis) is most common in children and young adults and tends to appear following an upper respiratory tract infection with beta-hemolytic streptococci. Eruptive psoriasis is characterized by many small erythematous, scaling papules and may also involve pustular lesions which are either localized to the palms and soles or may be generalized and associated with fever, malaise, diarrhea, and arthralgias.

In about 50% of all psoriasis cases the disease involves punctate pitting, nail thickening or subungual hyperkeratosis of the fingernails. On the other hand, 5-10% of psoriasis cases suffer from a joint disease, including a single or a few small joints (in 70% of the cases), seronegative rheumatoid arthritis-like disease, distal interphalangeal joints, severe destructive arthritis with the development of "arthritis mutilans", and a joint disease which is limited to the spine.

The treatment offered to psoriasis patients depends on the severity of the disease. While the less severe cases can be relieved using pomades or emollient creams which keep the skin hydrated, the more moderate cases of psoriasis are usually treated with topical formulations containing corticosteroids which are either applied underneath an occlusive covering made of cellophane or polyethylene, or incorporated into an adhesive bandage. However, depending on the affected area, applying such topical formulations represent a practical problem for the treated patients, especially during the day.

The more severe cases of psoriasis are treated by systemic therapies including methotrexate, cyclosporin A and retinoids. However, the use of such agents in the treatment of psoriasis is limited by severe side effects and the significant potential of nephrotoxicity, hypertension and liver toxicity.

There is thus a widely recognized need for, and it would be highly advantageous to have, methods and compositions for treating psoriasis devoid of the above limitations.

SUMMARY OF THE INVENTION

According to one aspect of the present invention there is provided a pharmaceutical composition comprising a cruciferous plant extract or an isothiocyanate and a pharmaceutical acceptable carrier formulated for topical application.

According to another aspect of the present invention there is provided a method of treating psoriasis in a subject comprising administering to the subject a composition including a cruciferous plant extract or an isothiocyanate thereby treating psoriasis in the subject.

According to yet another aspect of the present invention there is provided a cosmetic composition comprising a cruciferous plant extract or an isothiocyanate and a physiologically acceptable carrier.

According to further features in preferred embodiments of the invention described below, the cruciferous plant is selected from the group consisting of rocket, broccoli, cabbage, watercress and radish.

According to still further features in the described preferred embodiments the rocket is *Eruca Sativa*.

According to still further features in the described preferred embodiments a concentration of the cruciferous plant extract in the pharmaceutical composition is in the range of 5-50%.

According to still further features in the described preferred embodiments a concentration of the cruciferous plant extract in the cosmetic composition is in the range of 5-50%.

According to still further features in the described preferred embodiments a concentration of the cruciferous plant extract in the pharmaceutical composition is about 15%.

According to still further features in the described preferred embodiments a concentration of the cruciferous plant extract in the cosmetic composition is about 15%.

According to still further features in the described preferred embodiments the cruciferous plant extract is an alcohol extract.

According to still further features in the described preferred embodiments the cruciferous plant extract is a polar extract.

According to still further features in the described preferred embodiments the isothiocyanate is selected from the group consisting of 2-Propenyl-isothiocyanate, 3-Butenyl-isothiocyanate, 2R-2-Hydroxy-3-butenyl-isothiocyanate, 2S-2-Hydroxy-3-butenyl-isothiocyanate, p-Hydroxy-benzyl-isothiocyanate, Benzyl-isothiocyanate, 4-Methyl-thiobutyl-isothiocyanate, 3-Methyl-sulfonyl-propyl-isothiocyanate and 4-Methyl-sulfinyl-butenyl-isothiocyanate.

According to still further features in the described preferred embodiments a concentration of the 4-Methyl-thiobutyl-isothiocyanate in the pharmaceutical composition is in the range of 1-20 µM.

According to still further features in the described preferred embodiments a concentration of the 4-Methyl-thiobutyl-isothiocyanate in the cosmetic composition is in the range of 1-20 µM.

According to still further features in the described preferred embodiments a concentration of the 4-Methyl-thio-butyl-isothiocyanate in the pharmaceutical composition is about 10 µM.

According to still further features in the described preferred embodiments a concentration of the 4-Methyl-thio-butyl-isothiocyanate in the cosmetic composition is about 10 µM.

According to still further features in the described preferred embodiments the composition further includes a carrier suitable for topical administration, injection, subcutaneous administration and/or intramuscle administration.

The present invention successfully addresses the shortcomings of the presently known configurations by providing pharmaceutical and cosmetic compositions suitable for treating psoriasis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

The file of this patent contains at least one drawing executed in color photograph. Copies of this patent with color photograph(s) will be provided by the Patent and Trademark Office upon request and payment of necessary fee.

Figure 1:
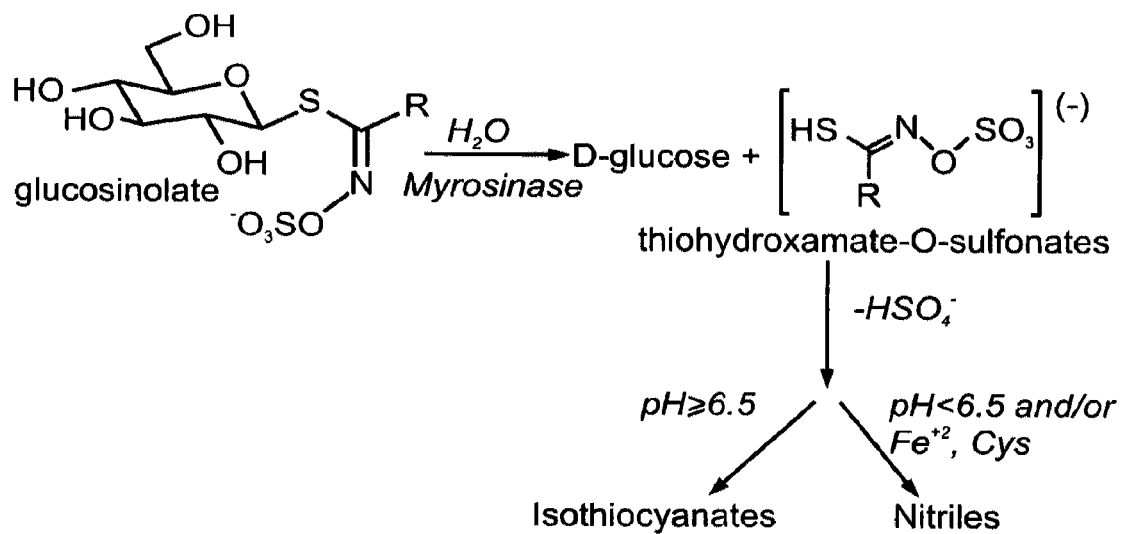

FIG. 1 is a schematic illustration depicting the hydrolysis of glucosinolates by Myrosinase to D-glucose and an intermediate molecule (thiohydroxamate-O-sulfonate) which further converts at pH≧6.5 to isothiocyanate. Adopted from Leoni O., et al., 1997; Bioorganic & Medicinal Chemistry 5: 1799-1806.

Figure 2A:
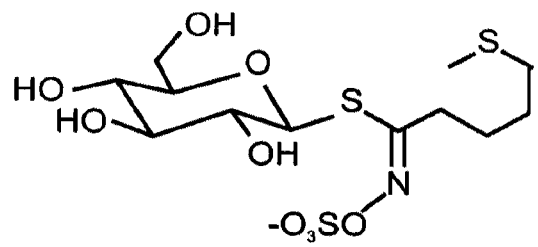
Figure 2B:

FIGS. 2a-b are schematic illustrations depicting the chemical structure of 4-(methylthio)butyl-isothiocyanate (FIG. 2a) and 4-(methylthio)butylglucosinolate (glucoerucin; FIG. 2b). Adopted from Fimognari C., et al., 2004; Investigational New Drugs 22: 119-129.

FIGS. 3a-d are photographs depicting the effect of the cruciferous plant extract composition of the present invention on a psoriasis lesion present on the back side of the leg of a 35 year-old-woman. A moderate-to-severe psoriasis lesion was treated twice a day for a time period of 4 weeks with the composition of the present invention. Shown is the psoriasis lesion before (FIGS. 3a-b) and after (FIGS. 3c-d) treatment with the composition of the present invention.

Figure 4B:
Figure 4C:
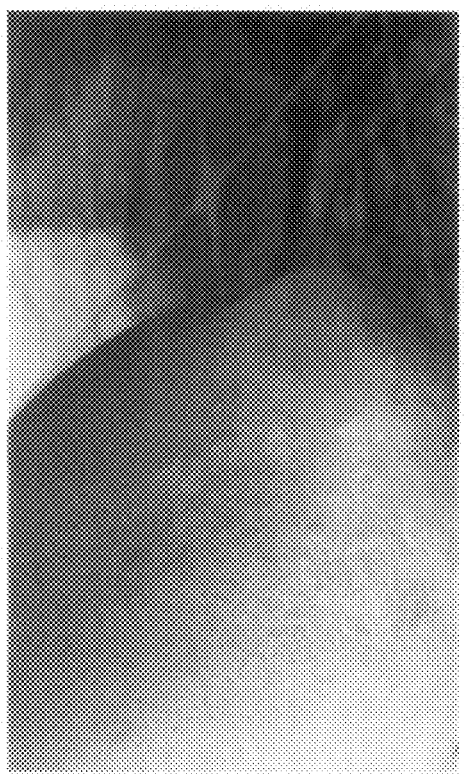
Figure 4A:
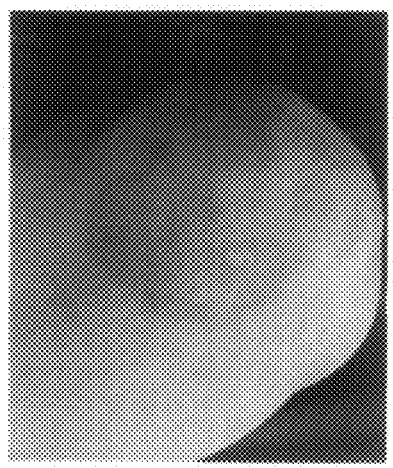
Figure 5B:
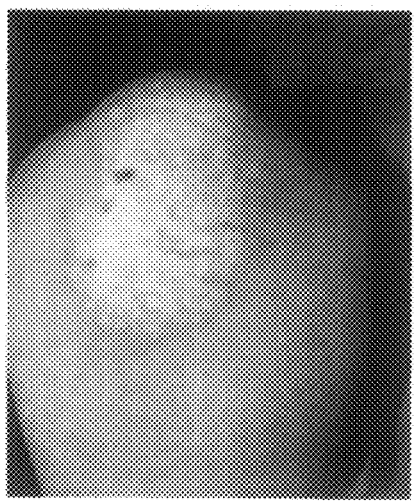
Figure 5D:
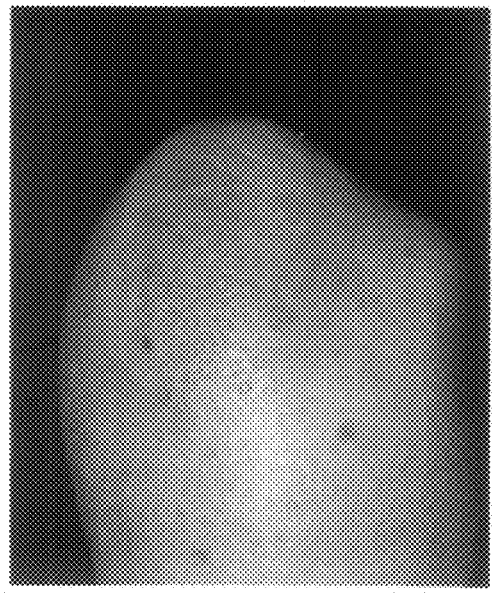
Figure 5A:
Figure 5C:

FIGS. 4a-c are photographs depicting the effect of the cruciferous plant extract composition of the present invention on a psoriasis lesion present on the elbow of a 35 year-old-woman. A non-severe to moderate psoriasis lesion was treated twice a day for a time period of 4 weeks with the composition of the present invention. Shown is the psoriasis lesion before (FIGS. 4a-b) and after (FIG. 4c) treatment with the composition of the present invention.

FIGS. 5a-d are photographs depicting the effect of the cruciferous plant extract composition of the present invention on a psoriasis lesion present on the elbow of a 71 year-old-woman who also suffers from type-II diabetes. A moderate-to-severe psoriasis lesion was treated twice a day for a time period of 4 weeks with the composition of the present invention. Shown is the psoriasis lesion before (FIGS. 5a-b) and after (FIGS. 5c-d) treatment with the composition of the present invention.

Figure 6A:
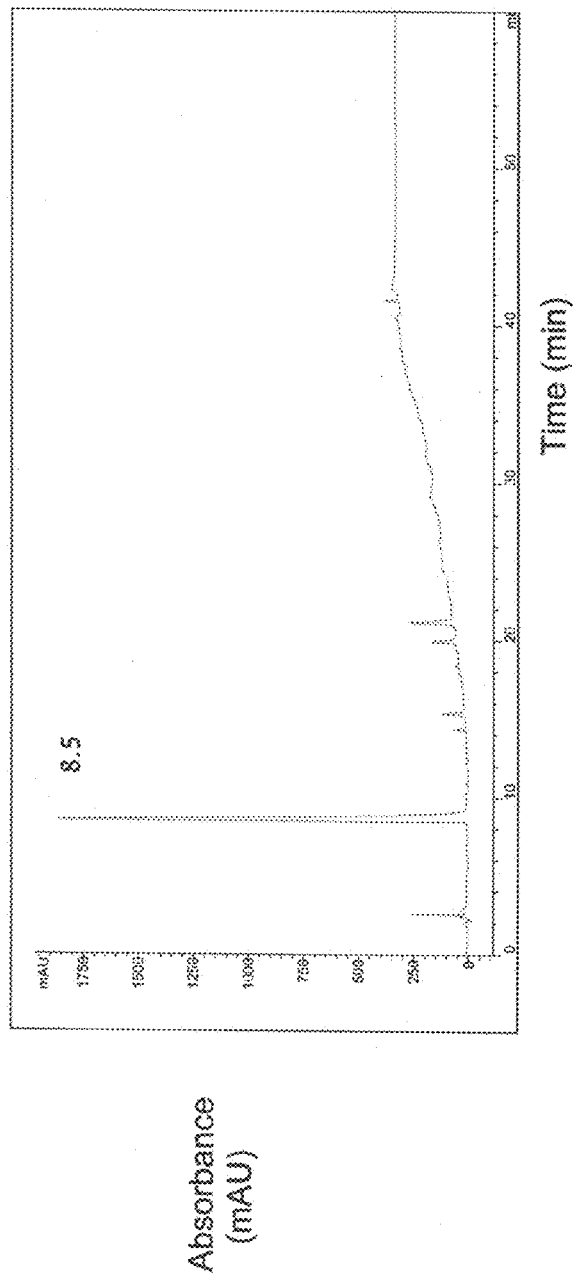
Figure 6B:
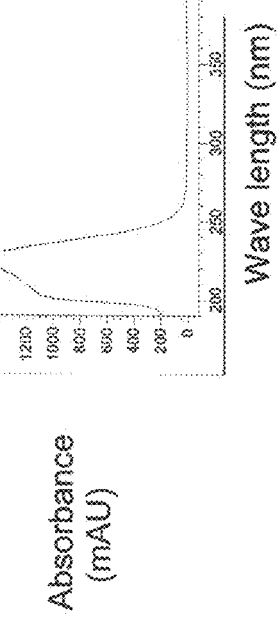
Figure 6C:
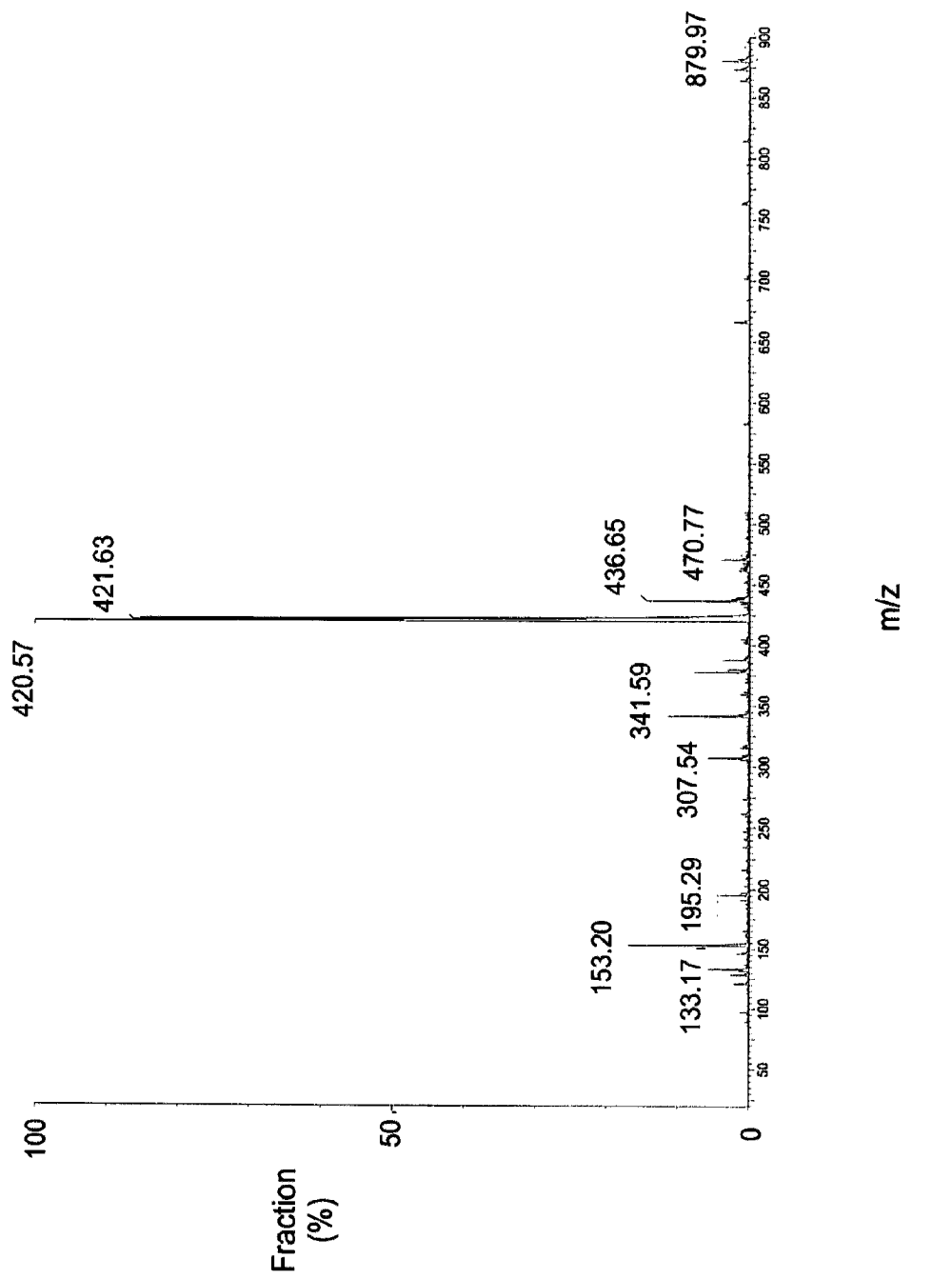

FIGS. 6a-c are graphs depicting high-pressure liquid chromatography (HPLC) (FIG. 6a), ultra violet (UV) spectrum (FIG. 6b) and liquid chromatography mass spectroscopy (LCMS) (FIG. 6c) analyses of the glucoerucin product extracted from the seeds of rocket. FIG. 6a—HPLC analysis of glucoerucin, absorbance [milli arbitrary units (mAU)] as a function of time [minutes (min)]; FIG. 6b—UV spectrum analysis, absorbance (mAU) as a function of wavelength (nm); Note the sharp peak appearing after 8.5 minutes in HPLC analysis (FIG. 6a) and the shape of the UV spectrum (FIG. 6b) characteristic to the glucoerucin product. FIG. 6c—LCMS analysis, the fraction of each peak (%) is presented as a function of mass to charge ratio (m/z). LCMS run in Scan ES⁻ mode. Note the peak obtained using the LCMS spectrum analysis depicting a molecular weight of 420.57 which is the expected m/z value of purified glucoerucin (i.e., 420.6 according to Bennett et al., 2004, J. Agri. Food Chem. 52:428-438).

Figure 7B:
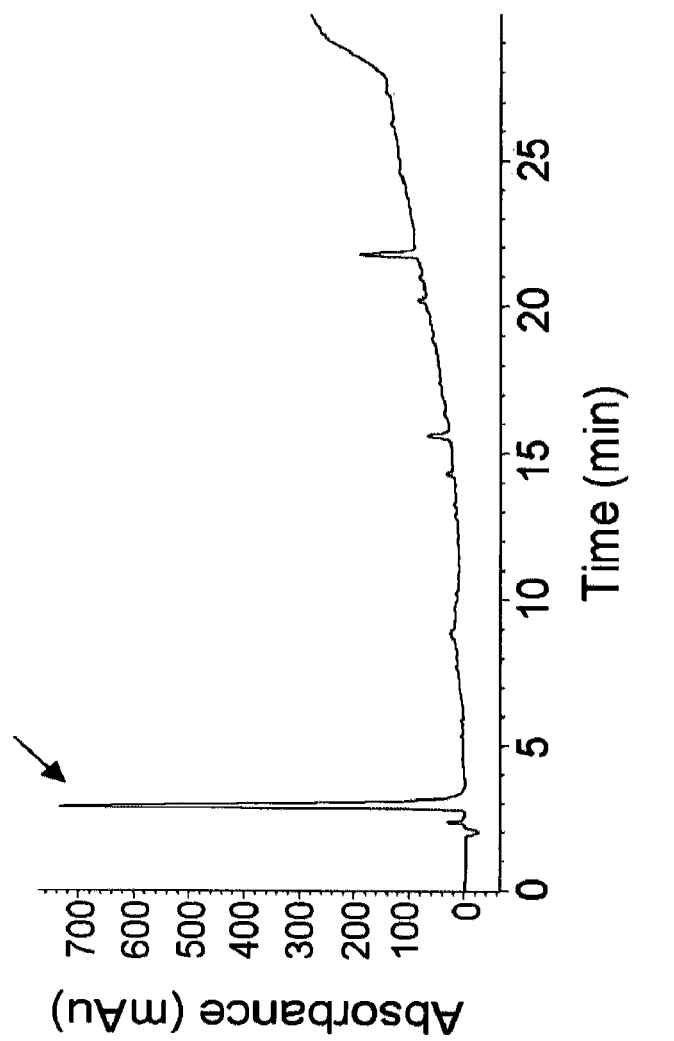

FIGS. 7a-b are graphs depicting HPLC analyses of glucoerucin before (FIG. 7a) or after (FIG. 7b) treatment with myrosinase. Note the peak of glucoerucin appearing after 8.5 minutes in HPLC (FIG. 7a, arrow) and the disappearance of such a peak following myrosinase treatment (FIG. 7b). The new peak at 2.5 minutes (marked with an arrow, FIG. 7b), represents the presence of myrosinase.

Figure 8A:
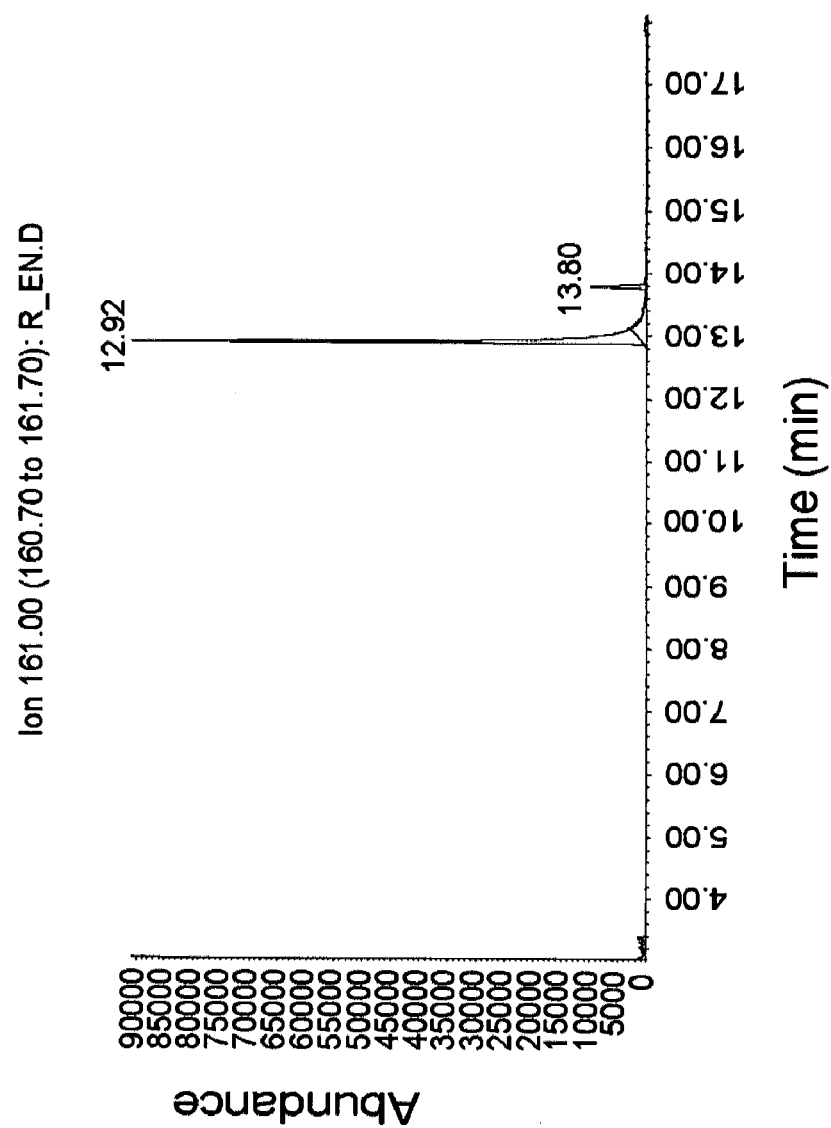
Figure 8B:
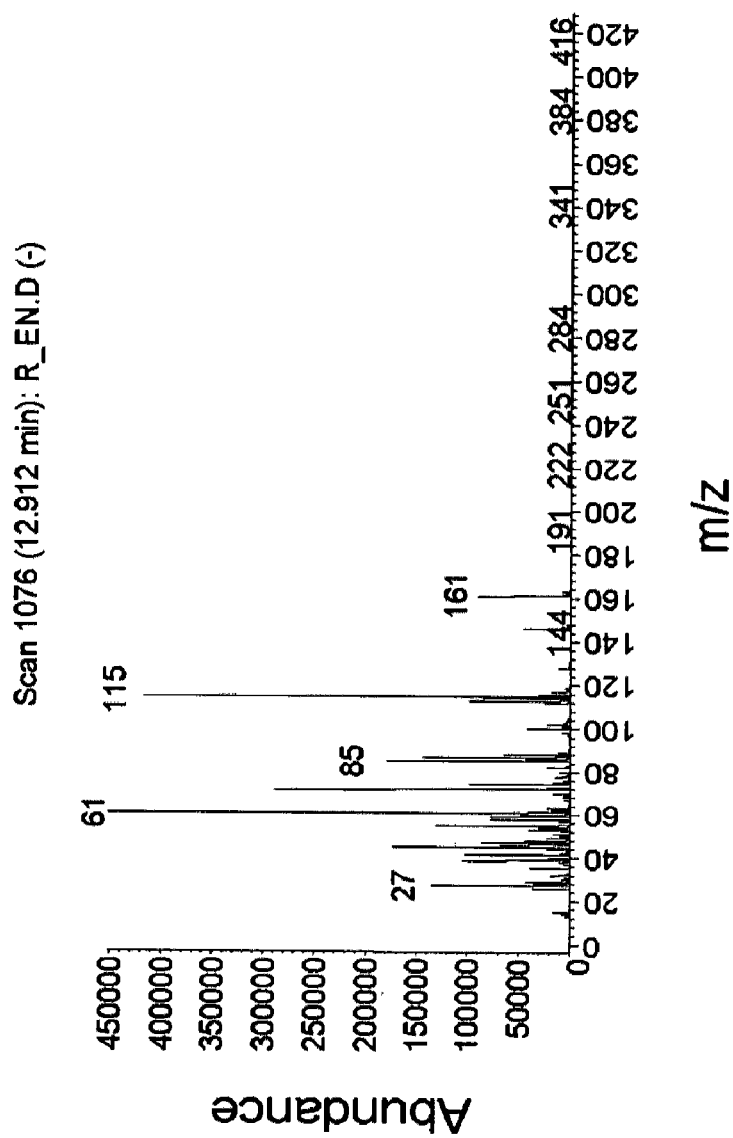

FIGS. 8a-b are graphs depicting Gas Chromatography (GC) (FIG. 8a) and mass spectroscopy (MS) analysis (FIG. 8b) of the purified 4-Methyl-thio-butyl-isothiocyanate, the product of myrosinase-hydrolyzed glucoerucin. FIG. 8a depicts the abundance (in arbitrary units) of glucoerucin extraction products following treatment with myrosinase as a function of retention time [min (minutes)] in GS. FIG. 8b depicts mass spectroscopy analysis of the product eluted at peak 12.912 minutes (abundance as a function of m/z). Note the m/z of 161 (corresponding to the MW of 4-Methyl-thio-butyl-isothiocyanate minus one hydrogen proton) and fragmentations in m/z of 115 (M-CH3-S) corresponding to the molecular ion of 4-Methyl-thio-butyl-isothiocyanate—the fragment of CH3-S.

Figure 9:
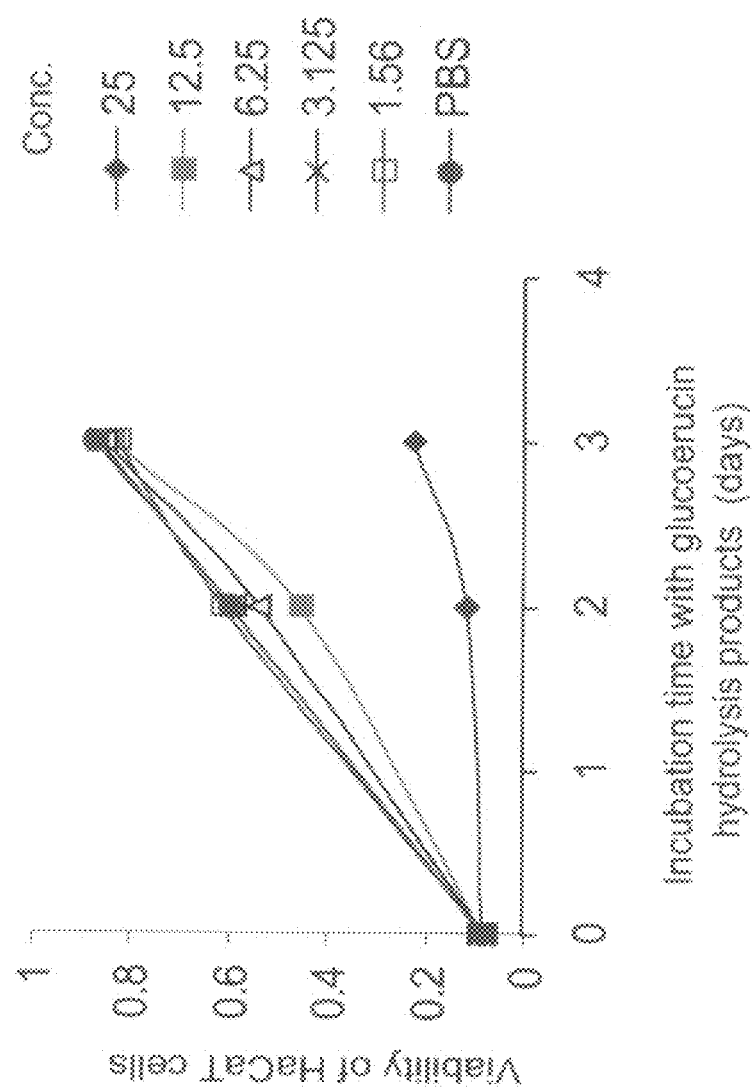

FIG. 9 is a graph depicting the viability of HaCaT cells (normal human keratinocytes) in the presence of the myrosinase hydrolysis products of glucoerucin of the present invention. HaCaT cells were incubated for four days in the presence of increasing concentrations (Conc.) of the glucoerucin hydrolysis products (which contain 4-Methyl-thio-butyl-isothiocyanate), i.e., 0 (PBS), 1.56, 3.125, 6.25, 12.5 and 25 µg/ml, and the effect of treatment was measured using the XTT cell cytotoxicity assay on samples of cells taken at the indicated time points (i.e., 0, 2 and 3 days following the addition of glucoerucin hydrolysis products to the culture medium). Note that while in the presence of 0-12.5 μg/ml of the glucoerucin hydrolysis products there was no significant effect on cell viability, in the presence of 25 μg/ml of the glucoerucin hydrolysis products about 75% of the cells were not viable.

DESCRIPTION OF THE PREFERRED EMBODIMENTS

The present invention is of pharmaceutical and cosmetic compositions including cruciferous plant extract or isothiocyanates and a physiological acceptable carrier useful for topical application which can be used to treat psoriasis. Specifically, the present invention can be used to treat psoriasis lesions of various degrees.

The principles and operation of the pharmaceutical compositions according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Psoriasis is a common, non-contagious, chronic skin disease affecting 2-4% of the Caucasian population. The main characteristics of the disease include the appearance of thick red zones on the skin which are frequently covered with silvery or whitish scaled eruptions and/or plaques of various sizes and/or degrees of pruritus.

While the precise cause of psoriasis is still unclear, mild cases of psoriasis are treated with various pomades or emollient creams which keep the skin hydrated. The more moderate cases of psoriasis are treated with topical formulations containing corticosteroids. On the other hand, the severe cases of psoriasis are treated by systemic therapies including agents which prevent skin cell growth (e.g., methotrexate), suppress the immunological system (e.g., cyclosporin A) or reduce the cohesiveness of abnormal hyperproliferative keratinocytes (e.g., retinoids). However, while the use of pomades and creams with or without corticosteroids exhibit only a moderate and temporary relief of psoriasis, the use of the systemic agents (e.g., methotrexate, cyclosporin A and retinoids) is often associated with severe side effects and significant potentials for nephrotoxicity, hypertension and/or liver toxicity.

Isothiocyanates are sulfur-containing compounds largely responsible for the typical flavor of cruciferous vegetables. Isothiocyanates are formed following the hydrolysis of glucosinolates by the myrosinase enzyme (See FIG. 1). The various glucosinolates molecules present in cruciferous plants (e.g., sinigrin, gluconapin, progoitrin, epi-progoitrin, sinalbin, glucotropaeolin, glucoerucin, glucocheirolin and glucoraphenin) are degraded to their specific isothiocyanate derivatives by the myrosinase enzyme present in plants or in the intestinal flora in the body. For example, grinding of cruciferous plants such as *Eruca Sativa* releases myrosinase which activates the hydrolysis of glucoerucin [4-(methylthio) butyl-glucosinolate] to 4-Methylthio-butylisiothiocyanate (FIGS. 2*a-b* and Fimognari C, et al., 2004, Investigational New Drugs 22: 119-129).

Prior art studies demonstrated that isothiocyanates isolated from seeds of cruciferous vegetables exhibit an inhibitory activity on K562 cells growth (Nastruzzi C et al., 2000, J. Agric. Food Chem. 48: 3572-5; Leoni, 0, et al., 1997, Bioorganic and Medicinal Chemistry, 5: 1799-1806) and can stimulate apoptosis and/or confer protection against DNA damage in human colon cell lines (Bonnesen C et al., 2001, Cancer Res. 61: 6120-30). Of the isothiocyanates tested, the most potent inhibitors of leukemic cell growth were 2-Propenyl-, Benzyl- and 4-(Methyl-thio)-butyl-isothiocyanates [Leoni, 1997 (Supra)].

While reducing the present invention to practice, the present inventor has uncovered that a cruciferous plant extract or an isothiocyanate present in such extract can be used to treat psoriasis.

As is shown in FIGS. 3-5 and is described in Example 1 of the Examples section which follows, application of a cream containing 15% of a *Eruca Sativa* plant extract on psoriasis lesions resulted in a significant improvement of the disease state, i.e., significant reductions in the width of the scaled lesion and the disappearance of the silvery plaques.

Thus, according to one aspect of the present invention there is provided method of treating psoriasis in a subject.

As used herein the phrase "psoriasis" refers to the presence of psoriasis lesions, i.e., patches of thick reddish skin and/or scaled eruptions which are often covered by silvery or whitish plaques, with variable degrees of pruritus. Psoriasis lesions can appear in any part of the human skin, mouth, genitalia and/or joints, including, but not limited to, elbows, knees, scalp, lower back, face, palms, soles of the feet, fingernails, toenails, soft tissues inside the mouth and/or genitalia, and/or joint inflammation which produces symptoms of arthritis.

The term "treating" refers to inhibiting or arresting the development of a disease, disorder or condition and/or causing the reduction, remission, or regression of a disease, disorder or condition. Those of skill in the art will understand that various methodologies and assays can be used to assess the development of a disease, disorder or condition, and similarly, various methodologies and assays may be used to assess the reduction, remission or regression of a disease, disorder or condition.

The phrase "subject" refers to any human being, male or female at any age who suffers from psoriasis at any stage and/or degree.

The method is effected by administering to the subject a composition including a cruciferous plant extract or an isothiocyanate (synthetic or isolated) thereby treating psoriasis in the subject.

The cruciferous plant used by the present invention can be any plant belonging to the Cruciferae plant family. Examples include, but are not limited to, rocket, broccoli, cabbage, watercress, and radish. According to presently preferred configurations, the cruciferous plant used by the present invention is *Eruca Sativa*, a type of rocket.

As used herein the phrase "cruciferous plant extract" refers to any extract made from a cruciferous plant. Plant extracts can be made by methods known in the arts including a polar extract such as an alcohol extract (e.g., ethanol, methanol, hexane, hydroalcohol, see for example Swanson R L et al., 2004, Biol. Bull. 206: 161-72) or a non-polar extract (e.g., isooctane, see for example, Ng LK and Hupe M. 2003, J. Chromatogr A. 1011: 213-9; Diwanay S, et al., 2004, J. Ethnopharmacol. 90: 49-55). For example, a plant extract can be made by placing a plant sample (e.g., leaves, seeds) in a mortar along with a small quantity of liquid (e.g., 10 ml of water, alcohol or an organic solvent for every 2 grams of plant sample) and grinding the sample thoroughly using a pestle. When the plant sample is completely ground, the plant extract is separated from the ground plant material via, centrifugation, filtering, cation-exchange chromatography, etc., and the collected liquid is further processed if need be (via a concentrating column etc), active ingredients can be separated from this extract via affinity chromatography, mass chromatography and the like.

Cruciferous plant extracts can be also obtained from a variety of commercial sources such as Gehrlicher (Eurasburg, Germany). For example, an alcohol extract of the *Eruca Sativa* can be purchased from a variety of manufacturers such as Gehrlicher (Eurasburg, Germany) and The Herbal Apothecary (Syston Leicester, England).

It will be appreciated that the concentration of the cruciferous plant extract in the composition of the present invention can vary between 0.01% to 99% depending on the severity of the psoriasis lesion to be treated. Preferably, the concentration of the cruciferous plant extract is between 5% to 80%, more preferably, between 5% to 70%, more preferably, between 5% to 50%, more preferably, between 5% to 30%. According to presently preferred configurations, the concentration of the cruciferous plant extract in the pharmaceutical composition of the present invention is about 15% (see Example 1 of the Examples section which follows).

The isothiocyanate used by the present invention can be any known isothiocyanate having the general formula: R—N=C=S, wherein R can be any compatible substituent such as, for example, aryl, cycloalkyl, alkyl, alkenyl, alkynyl, heteroaryl, heteroalicyclic, hydroxy, thiohydroxy, halo and the like.

As used herein, the term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 6 carbon atoms. The alkyl group may be substituted or unsubstituted. When substituted, the substituent group can be, for example, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonamide, phosphonyl, phosphinyl, phosphonium, carbonyl, thiocarbonyl, thiocarboxy, urea, thiourea, 0-carbamyl, N-carbamyl, O-thio-carbamyl, N-thiocarbamyl, C-amido, N-amido, C-carboxy, O-carboxy, guanyl, guanidino, and amino.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonamide, phosphonyl, phosphinyl, phosphonium, carbonyl, thiocarbonyl, thiocarboxy, urea, thiourea, O-carbamyl, N-carbamyl, O-thiocarbamyl, N-thiocarbamyl, C-amido, N-amido, C-carboxy, O-carboxy, guanyl, guanidino, and amino.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonamide, phosphonyl, phosphinyl, phosphonium, carbonyl, thiocarbonyl, thiocarboxy, urea, thiourea, O-carbamyl, N-carbamyl, O-thiocarbamyl, N-thiocarbamyl, C-amido, N-amido, C-carboxy, O-carboxy, guanyl, guanidino, and amino.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonamide, phosphonyl, phosphinyl, phosphonium, carbonyl, thiocarbonyl, thiocarboxy, urea, thiourea, O-carbamyl, N-carbamyl, O-thiocarbamyl, N-thiocarbamyl, C-amido, N-amido, C-carboxy, O-carboxy, guanyl, guanidino, and amino.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonamide, phosphonyl, phosphinyl, phosphonium, carbonyl, thiocarbonyl, thiocarboxy, urea, thiourea, O-carbamyl, N-carbamyl, O-thiocarbamyl, N-thiocarbamyl, C-amido, N-amido, C-carboxy, O-carboxy, guanyl, guanidino, and amino. Representative examples are piperidine, piperazine, tetrahydro furane, tetrahydropyrane, morpholino and the like.

A "hydroxy" group refers to an —OH group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to an —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R' group, where R' is hydrogen, alkyl, alkenyl, cycloalkyl, aryl, heteroaryl (bonded through a ring carbon) or heteroalicyclic (bonded through a ring carbon) as defined herein.

A "thiocarbonyl" group refers to a —C(=S)—R' group, where R' is as defined herein for R'.

A "C-carboxy" group refers to a —C(=O)—O—R' groups, where R' is as defined herein.

An "O-carboxy" group refers to an R'C(=O)—O— group, where R' is as defined herein.

A "halo" group refers to fluorine, chlorine, bromine or iodine.

A "trihaloalkyl" group refers to an alkyl group substituted by three halo groups, as defined herein.

A "sulfinyl" group refers to an —S(=O)—R' group, where R' is as defined herein.

A "sulfonyl" group refers to an —S(=O)$_2$—R' group, where R' is as defined herein.

An "S-sulfonamide" group refers to a —S(=O)$_2$—NR'R" group, with R' as defined herein and R" as defined herein for R'.

An "N-sulfonamido" group refers to an R'S(=O)$_2$—NR" group, where R' and R" are as defined herein.

An "O-carbamyl" group refers to an —OC(=O)—NR'R" group, where R' and R" are as defined herein.

An "N-carbamyl" group refers to an R"OC(=O)—NR'— group, where R' and R" are as defined herein.

An "O-thiocarbamyl" group refers to an —OC(=S)—NR'R" group, where R' and R" are as defined herein.

An "N-thiocarbamyl" group refers to an R"OC(=S)NR'— group, where R' and R" are as defined herein.

An "amino" group refers to an —NR'R" group where R' and R" are as defined herein.

A "C-amido" group refers to a —C(=O)—NR'R" group, where R' and R" are as defined herein.

An "N-amido" group refers to an R'C(=O)—NR" group, where R' and R" are as defined herein.

An "urea" group refers to an —NR'C(=O)—NR"R'" group, where R' and R" are as defined herein and R'" is defined as either R' or R".

A "guanidino" group refers to an —R'NC(=N)—NR"R'" group, where R', R" and R'" are as defined herein.

A "guanyl" group refers to an R'R"NC(=N)— group, where R' and R" are as defined herein.

A "nitro" group refers to an —NO$_2$ group.

A "cyano" group refers to a —C≡N group.

The term "phosphonyl" describes a —O—P(=O)(OR')— group, with R' as defined hereinabove.

The term "phosphinyl" describes a —PR'— group, with R' as defined hereinabove.

The term "phosphonium" describes a —P+R'R", where R' and R" are as defined hereinabove.

The term "thiourea" describes a —NR'—C(=S)—NR'— group, with R' and R" as defined hereinabove.

The term "hydrazine" described a NR'—NR" group, with R' and R" as defined hereinabove.

Examples of isothiocyanates which can be utilized by the present invention, include, but are not limited to, 2-Propenyl-isothiocyanate, 3-Butenyl-isothiocyanate (C$_5$H$_7$NS), 2R-2-Hydroxy-3-butenyl-isothiocyanate, 2S-2-Hydroxy-3-butenyl-isothiocyanate, p-Hydroxy-benzyl-isothiocyanate, Benzyl-isothiocyanate, 4-Methyl-thio-butyl-isothiocyanate, 3-Methyl-sulfonyl-propyl-isothiocyanate, 4-Methyl-sulfinyl-butenyl-isothiocyanate, 2-Phenylethyl isothiocyanate (C$_6$H$_5$CH$_2$CH$_2$NCS), Phenethyl isothiocyanate (C$_6$H$_5$CH$_2$CH$_2$NCS), 4-(Boc-aminomethyl)phenyl isothiocyanate (C$_{13}$H$_{16}$N$_2$O$_2$S), Fluorescein 5(6)-isothiocyanate (C$_{21}$H$_{11}$NO$_5$S), p-Tolyl isothiocyanate (CH$_3$C$_6$H$_4$NCS), 4-Azidophenyl isothiocyanate (N$_3$C$_6$H$_4$NCS), 4-Bromophenyl isothiocyanate (BrC$_6$H$_4$NCS), 4-Chlorophenyl isothiocyanate (ClC$_6$H$_4$NCS), 4-Isothiocyanato-but-1-ene (C$_5$H$_7$NS), 4-Brom-2-fluorbenzylisothiocyanate (C$_8$H$_5$BrFNS), 3-Brom-4-fluorbenzylisothiocyanate (C$_8$H$_5$BrFNS), 5-Brom-2-fluorbenzylisothiocyanate (C$_8$H$_5$BrFNS), 4-Chlor-2-fluorbenzylisothiocyanate (C$_8$H$_5$ClFNS), 3-Chlorbenzylisothiocyanate (C$_8$H$_6$ClNS), 4-(Trifluormethoxy)-benzylisothiocyanate (C$_9$H$_6$F$_3$NOS), 2,6-Difluorbenzylisothiocyanate (C$_8$H$_5$F$_2$NS). For additional chemical structures see FIG. 2a.

Such isothiocyanates can be isolated from the cruciferous plant extract of the present invention by subjecting glucosinolates present in such plants to hydrolysis by the myrosinase enzyme. Myrosinase can be isolated from ripe seeds of white mustard (Sinapis alba L.) by concanavalin A affinity chromatography and chromatofocusing as described elsewhere (Palmieri S., et al., 1986, J. Agric. Food Chem. 34: 138; Palmieri S., et al., 1982, Anal. Biochem. 123: 320). Glucosinolates can be isolated following the methods described by Thies W (Fat Sci. Technol. 1988, 8: 311) or Visentin M (J. Agric. Food Chem. 1992 40: 1687), and the isothiocyanates can be further isolated as described elsewhere [Iori R., et al., 1999, Bioorg. Med. Chem. Lett. 9: 1047-1048; Visentin M., et al., 1991, J. Agric. Food Chem. 40: 1687-1691; EEC Regulation No. 1864/90: Enclosure VIII. Offic. J. Eur. Commun. LI 70: 27-34, 1990; Pessina A., et al., 1990, Arch. Biochem. Biophys. 280: 383-389; and Fimognari, 2004 (Supra)].

For example, 4-methyl-thio-butyl-isothiocyanate can be obtained by the enzymatic hydrolysis of glucoerucin that is extracted from Eruca sativa as described in Example 2 of the Examples section which follows. Such isothiocyanate was found capable of inhibiting cell proliferation of hyperproliferative cancerous cells (e.g., Jurkat T-leukemia cells) and was found less cytotoxic to normal keratinocyte (e.g., HaCaT cells).

The isothiocyanates used by the present invention can be also purchased from chemical suppliers such as Merck (Daemstadt, Germany), Sigma (Sigma, St Louis, Mo., USA).

The concentration of isothiocyanate [e.g., 4-(methylthio)-butyl-isothiocyanate] in the composition of the present invention can be between 1-20 μM, more preferably, 5-15 μM, most preferably, about 10 μM.

The composition including the cruciferous plant extract or isothiocyanate of the present invention can be administered to the subject per se, or in a pharmaceutical or a cosmetic composition where it is mixed with suitable carriers or excipients.

Preferably, the composition of the present invention further includes a carrier suitable for topical administration, intramuscular injection, subcutaneous administration, transmucosal (e.g., intragenitalia or intramouth) and/or intradermal administration as is further described hereinbelow.

As used herein a "pharmaceutical composition" or a "cosmetic composition" refers to a preparation of one or more of the active ingredients described herein with other chemical components such as pharmaceutically or physiologically suitable carriers and excipients. The purpose of a pharmaceutical composition or cosmetic composition is to facilitate administration of the active ingredient to an organism.

Herein the term "active ingredient" refers to the cruciferous plant extract or the isothiocyanate of the present invention accountable for the biological effect (i.e., treating psoriasis).

Hereinafter, the phrase "pharmaceutical acceptable carrier" or "physiological acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical or cosmetic composition to further facilitate administration of an active ingredient. Examples, without limitation, of excipients include calcium carbonate, calcium phosphate, various sugars and types of starch, cellulose derivatives, gelatin, vegetable oils and polyethylene glycols.

The pharmaceutical or cosmetic composition of the present invention may be applied in a local manner, for example, via administration of the composition directly into a tissue region of a patient. Suitable routes of administration of pharmaceutical compositions may, for example, include topical, subcutaneous, intramuscular, intradermal, intragenitalia and intramouth administration.

Pharmaceutical or cosmetic composition of the present invention may be manufactured by processes well known in the art, e.g., by means of conventional mixing, dissolving, granulating, dragee-making, levigating, emulsifying, encapsulating, entrapping or lyophilizing processes.

Pharmaceutical or cosmetic composition for use in accordance with the present invention thus may be formulated in conventional manner using one or more physiologically acceptable carriers comprising excipients and auxiliaries, which facilitate processing of the active ingredients into preparations. Proper formulation is dependent upon the administration approach chosen.

For injection, the active ingredients of the pharmaceutical composition may be formulated in aqueous solutions, preferably in physiologically compatible buffers such as Hank's solution, Ringer's solution, or physiological salt buffer. For transmucosal (e.g., intragenitalia and intramouth) administration, penetrants appropriate to the barrier to be permeated are used in the formulation. Such penetrants are generally known in the art. For Alternatively, the active ingredient may be in a powder form for constitution with a suitable vehicle, e.g., sterile, pyrogen-free water based solution, before use.

Determination of a therapeutically effective amount is well within the capability of those skilled in the art, especially in light of the detailed disclosure provided herein.

For any preparation used in the method of the invention, the therapeutically effective amount or dose can be estimated initially from in vitro assays. In addition, a dose can be formulated in tissue cultures systems or in animal models to achieve a desired concentration or titer. Such information can be used to more accurately determine useful doses in humans.

Depending on the severity of the disease (e.g., the total affected area, the type and degree of the psoriasis lesion, and the involvement of other tissues such as joints) and the responsiveness of the skin or joint involves, dosing can be of a single or a plurality of administrations, with course of treatment lasting from several days to several weeks or until cure is effected or diminution of the skin disorder is achieved.

The amount of a composition to be administered will, of course, be dependent on the subject being treated, the severity of the affliction, the manner of administration, the judgment of the prescribing physician, etc.

Following is a description of formulations incorporating the composition of the present invention which includes the cruciferous plant extract or isothiocyanate of the present invention for topical application.

As used herein the phrase "topical" refers to application of the composition of the present invention on the surface of a body, i.e., skin, scalp, hair, nails and the like.

Since the pharmaceutical or cosmetic compositions of the present invention is utilized in vivo, the composition is preferably of high purity and substantially free of potentially harmful contaminants, e.g., at least National Food (NF) grade, generally at least analytical grade, and preferably at least pharmaceutical grade. To the extent that a given compound must be synthesized prior to use, such synthesis or subsequent purification shall preferably result in a product that is substantially free of any potentially contaminating toxic agents that may have been used during the synthesis or purification procedures.

The following sections describe by way of examples the various components of pharmaceutical or cosmetic compositions of the present invention stating with the active ingredient.

Active Ingredients

The active ingredients, i.e., the cruciferous plant extract or isothiocyanate described hereinabove are included in the pharmaceutical or cosmetic composition of the present invention at a concentration suitable for achieving the biological effect (i.e., treating psoriasis). For example, as is mentioned hereinabove, the cruciferous plant extract can be included at a concentration of 5-50%, more preferably, at a concentration of 15%, and the isothiocyanate [e.g., 4-(methylthio)-butyl-isothiocyanate] can be included at a concentration of 1-20 µM, more preferably, 10 µM.

The pharmaceutical or cosmetic composition is preferably buffered to a pH of 6.5-7.0 since myrosinase, the enzyme that degrades the glucosinolate of the cruciferous plant extract is active at pH 6.5 [Leoni, 1997 (Supra)].

Any buffer capable of maintaining a pH of 6.5-7.0 may be employed. Examples for suitable buffers which may be used by the pharmaceutical or cosmetic composition of the present invention include, but are not limited to, phosphate buffer, Tris-HCl buffer, and the like.

In addition to the pharmaceutically effective amount of an agent disclosed herein, the pharmaceutical or cosmetic compositions of this aspect of the present invention also includes a dermatologically acceptable carrier.

The phrase "dermatologically acceptable carrier", refers to a carrier which is suitable for topical application onto the skin, i.e., keratinous tissue, has good aesthetic properties, is compatible with the active agents of the present invention and any other components, and is safe and non-toxic for use in mammals. An effective amount of carrier is selected from a range of about 50% to about 99.99%, preferably from about 80% to about 99.9%, more preferably from about 90% to about 98%, and most preferably from about 90% to about 95%, by weight, of the composition.

In order to enhance the percutaneous absorption of the active ingredients (e.g., the cruciferous plant extract or isothiocyanate of the present invention), one or more of a number of agents can be added to the pharmaceutical or cosmetic compositions including, but not limited to, dimethylsulfoxide, dimethylacetamide, dimethylformamide, surfactants, azone, alcohol, acetone, propylene glycol and polyethylene glycol.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion or an aerosol. As will be understood by the skilled artisan, a given component will distribute primarily into either the water or oil/silicone phase, depending on the water solubility/dispersibility of the component in the composition.

Emulsions according to the present invention generally contain a pharmaceutically effective amount of an agent disclosed herein and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are described in, for example, U.S. Pat. No. 3,755,560, issued to Dickert, et al. Aug. 28, 1973; U.S. Pat. No. 4,421,769, issued to Dixon, et al., Dec. 20, 1983; and McCutcheon's Detergents and Emulsifiers, North American Edition, pages 317-324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less. The emulsion may also contain an anti-foaming agent to minimize foaming upon application to the keratinous tissue. Anti-foaming agents include high molecular weight silicones and other materials well known in the art for such use.

One type of emulsion is a water-in-silicone emulsion. Water-in-silicone emulsions contain a continuous silicone phase and a dispersed aqueous phase. Preferred water-in-silicone emulsions of the present invention comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase may contain a polyorganosiloxane oil. A preferred water-in-silicone emulsion system is formulated to provide an oxidatively stable vehicle for delivery of a pharmaceutically effective amount of an agent disclosed herein. The continuous silicone phase of these preferred emulsions comprises between about 50% and about 99.9% by weight of organopolysiloxane oil and less than about 50% by weight of a non-silicone oil. In an especially preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and most preferably less than about 2%, by weight of the continuous silicone phase. These useful emulsion systems may provide more oxidative stability over extended periods of time than comparable water-in-oil emulsions containing lower concentrations of the polyorganosiloxane oil. Concentrations of non-silicone oils in the continuous silicone phase are minimized or avoided altogether so as to possibly further enhance oxidative stability of the active compound of the invention in the compositions. Water-in-silicone emulsions of this type are described in U.S. Pat. No. 5,691,380 to Mason et al., issued Nov. 25, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100 degrees Celsius. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes, which are known to those skilled in the art and commercially available.

The continuous silicone phase may contain one or more non-silicone oils. Concentrations of non-silicone oils in the continuous silicone phase are preferably minimized or avoided altogether so as to further enhance oxidative stability of the pharmaceutically effective agent in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

Useful topical compositions of the present invention comprise from about 30% to about 90%, more preferably from about 50% to about 85%, and most preferably from about 70% to about 80% of a dispersed aqueous phase. The term "dispersed phase" is well-known to one skilled in the art it implies that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore. The aqueous phase can be water, or a combination of water and one or more water soluble or dispersible ingredients. Non-limiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention typically comprise from about 25% to about 90%, preferably from about 40% to about 80%, more preferably from about 60% to about 80%, water in the dispersed aqueous phase by weight of the composition.

The water-in-silicone emulsions of the present invention preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, e.g., organically modified organopolysiloxanes, also known to those skilled in the art as silicone surfactants, non-silicon-containing emulsifiers, and mixtures thereof, known by those skilled in the art for use in topical personal care products.

Useful emulsifiers include a wide variety of silicone emulsifiers. These silicone emulsifiers are typically organically modified organopolysiloxanes, also known to those skilled in the art as silicone surfactants. Suitable emulsifiers are described, for example, in McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Other preferred topical carriers include oil-in-water emulsions, having a continuous aqueous phase and a hydrophobic, water-insoluble phase ("oil phase") dispersed therein. Examples of suitable carriers comprising oil-in-water emulsions are described in U.S. Pat. No. 5,073,371 to Turner, D. J. et al., issued Dec. 17, 1991, and U.S. Pat. No. 5,073,372, to Turner, D. J. et al., issued Dec. 17, 1991. An especially preferred oil-in-water emulsion, containing a structuring agent, hydrophilic surfactant and water, is described in detail hereinafter.

A preferred oil-in-water emulsion comprises a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention comprise from about 0.5% to about 20%, more preferably from about 1% to about 10%, most preferably from about 1% to about 5%, by weight of the composition, of a structuring agent. The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

A wide variety of anionic surfactants are also useful herein. See, e.g., U.S. Pat. No. 3,929,678, to Laughlin et al., issued Dec. 30, 1975. In addition, amphoteric and zwitterionic surfactants are also useful herein.

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water. Suitable surfactants include any of a wide variety of known cationic, anionic, zwitterionic, and amphoteric surfactants. See, McCutcheon's. Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al. issued to Dec. 20, 1983; and U.S. Pat. No. 3,755,560. The exact surfactant chosen depends upon the pH of the composition and the other components present. Preferred are cationic surfactants, especially dialkyl quaternary ammonium compounds, examples of which are described in U.S. Pat. No. 5,151,209 to McCall et al. issued to Sep. 29, 1992; U.S. Pat. No. 5,151,210 to Steuri et al., issued to Sep. 29, 1992; U.S. Pat. No. 5,120,532; U.S. Pat. No. 4,387,090; U.S. Pat. No. 3,155,591; U.S. Pat. No. 3,929,678; U.S. Pat. No. 3,959,461; McCutcheon's, Detergents & Emulsifiers (North American edition 1979) M.C. Publishing Co.; and Schwartz, et al., Surface Active Agents, Their chemistry and Technology, New York: Interscience Publishers, 1949.

Alternatively, other useful cationic emulsifiers include amino-amides. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl(myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

The preferred oil-in-water emulsion comprises from about 25% to about 98%, preferably from about 65% to about 95%, more preferably from about 70% to about 90% water by weight of the topical carrier.

The pharmaceutical or cosmetic composition of the present invention can be formulated in any of a variety of forms utilized by the pharmaceutical or cosmetic industry for skin application including solutions, lotions, sprays, creams, ointments, salves, gels, etc., as described below.

Preferably, the pharmaceutical or cosmetic composition of the present invention is formulated viscous enough to remain on the treated skin area, does not readily evaporate, and/or is not easily removed by rinsing with water, but rather is removable with the aid of soaps, cleansers and/or shampoos.

Methods for preparing compositions having such properties are well known to those skilled in the art, and are described in detail in Remington's Pharmaceutical Sciences, 1990 (supra); and Pharmaceutical Dosage Forms and Drug Delivery Systems, 6th ed., Williams & Wilkins (1995).

The topical compositions of the subject invention, including but not limited to lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. See, e.g., Sagarin, Cosmetics, Science and Technology, 2nd Edition, Vol. 1, pp. 3243 (1972), which contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the present invention generally comprise a solution carrier system and one or more emollients. Lotions typically comprise from about 1% to about 20%, preferably from about 5% to about 10% of emollient; from about 50% to about 90%, preferably from about 60% to about 80% water; and a pharmaceutically effective amount of an agent described herein. A cream typically comprises from about 5% to about 50%, preferably from about 10% to about 20% of emollient; from about 45% to about 85%, preferably from about 50% to about 75% water; and a pharmaceutically effective amount of an agent described herein.

The topically applied pharmaceutical or cosmetic composition of the present invention may also include additional components which are added, for example, in order to enrich the cosmetic compositions with fragrance and skin nutrition factors.

Such components are selected suitable for use on human keratinous tissue without inducing toxicity, incompatibility, instability, allergic response, and the like within the scope of sound medical judgment. In addition, such optional components are useful provided that they do not unacceptably alter the benefits of the active compounds of the invention.

The CTFA Cosmetic Ingredient Handbook, Second Edition (1992) describes a wide variety of non-limiting cosmetic ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyfhizinate), skin treating agents, thickeners, and vitamins and derivatives thereof.

The pharmaceutical or cosmetic composition of the present invention can be applied directly to the skin. Alternatively, it can be delivered via normal skin application by various transdermal drug delivery systems which are known in the art, such as transdermal patches that release the composition into the skin in a time released manner. Other drug delivery systems known in the arts include pressurized aerosol bottle, iontophoresis or sonophoresis. Iontophoresis is employed to increase skin permeability and facilitate transdermal delivery. U.S. Pat. Nos. 5,667,487 and 5,658,247 discloses an ionosonic apparatus suitable for the ultrasonic-iontophoretically mediated transport of therapeutic agents across the skin. Alternatively, or in addition, liposomes or micelles may also be employed as a delivery vehicle.

Since psoriasis lesions often affect the skin of the scalp, the pharmaceutical or cosmetic composition of the present invention further includes emollients, surfactants and/or conditioners which are suitable for use on the scalp skin and hair.

The emollients include, but are not limited to, hydrocarbon oils and waxes, such as mineral oil, petrolatum, and the like, vegetable and animal oils and fats, such as olive oil, palm oil, castor oil, corn oil, soybean oil, and the like, and lanolin and its derivatives, such as lanolin, lanolin oil, lanolin wax, lanolin alcohols, and the like. Other emollients include esters of fatty acids having 10 to 20 carbon atoms, such as including myristic, stearic, isostearic, palmitic, and the like, such as methyl myristate, propyl myristate, butyl myristate, propyl stearate, propyl isostearate, propyl palmitate, and the like. Other emollients include fatty acids having 10 to 20 carbon atoms, including stearic, myristic, lauric, isostearic, palmitic, and the like. Emollients also include fatty alcohols having ten to twenty carbon atoms, such as cetyl, myristyl, lauryl, isostearyl, stearyl and the like.

Although some are water soluble, polyhydric alcohols and polyether derivatives are included as emollients, including glycols, glycerol, sorbitol, polyalkylene glycols and the like, such as propylene glycol, dipropylene glycol, polyethylene glycol 200-500, and the like. The water soluble examples are preferred.

An emulsifier/surfactant is preferably utilized when formulating the pharmaceutical or cosmetic composition of the present invention for use on hair.

Examples of surfactants include, but are not limited to, spolyoxyalkylene oxide condensation products of hydrophobic alkyl, alkene, or alkyl aromatic functional groups having a free reactive hydrogen available for condensation with hydrophilic alkylene oxide, polyethylene oxide, propylene oxide, butylene oxide, polyethylene oxide or polyethylene glycol Particularly effective are the condensation products of octylphenol with about 7 to about 13 moles of ethylene oxide, sold by the Rohm & Haas Company under their trademark TRITON 100® series products.

Other ingredients such as, fragrances, stabilizing agents, dyes, antimicrobial agents, antibacterial agents, anti agglomerates, ultraviolet radiation absorbers, and the like are also included in the composition of the present invention which is formulated for use on hair.

A conditioner agent stable to acid hydrolysis, such as a silicone compound having at least one quaternary ammonium moiety along with an ethoxylated monoquat is preferably also utilized in order to stabilize and optionally thicken the composition of the present invention which is formulated for use on hair.

An optional thickener also can be included to improve composition esthetics and facilitate application of the composition to the hair. Nonionic thickeners in an amount of 0% to about 3% by weight are preferred. Exemplary thickeners are methylcellulose, hydroxybutyl methylcellulose, hydroxypropylcellulose, hydroxypropyl methylcellulose, hydroxyethyl ethylcellulose and hydroxyethylcellulose, di(hydrogenated tallow)phthalic acid amide, crosslinked maleic anhydride-methyl vinyl ether copolymer, guar gum, xanthan gum and gum arabic.

The carrier of the conditioning composition is predominantly water, but organic solvents also can be included in order to facilitate manufacturing of the composition or to provide esthetic properties, such as viscosity control. Suitable solvents include the lower alcohols like ethyl alcohol and isopropyl alcohol; glycol ethers, like 2-butoxyethanol, ethylene glycol monoethyl ether, propylene glycol and diethylene glycol monoethyl ether or monomethyl ether; and mixtures thereof. Non-aqueous solvents can be present in the conditioning composition of the present invention in an amount of about 1% to about 50%, and in particular about 5% to about 25%, by weight of the total weight of the carrier in the composition.

Non-limiting conditioning agents which may be used in opaque conditioners include: stearyltrimethylammonium chloride; behenetrimethylammonium chloride; cetrimonium bromide; soytrimonium chloride; tallowtrimonium chloride; dihyrogenatedtallowedimethylammonium chloride; behentrimethylammonium methosulfate; Peg-2 Oleammonium chloride; dihyrogenatedtallowedimethylammonium bromide; dihyrogenatedtallowedimethylammonium methosulfate; palmityltrimethylammonium chloride; hydrogenated tallowtrimethylammonium chloride; hydrogenated tallowtrimethylammonium bromide; dicetyidimethylammonium chloride; distearyldimethylammonium chloride; dipalmityidimethylammonium chloride; hydrogenated tallowtrimethylammonium methosulfate; cetrimonium tosylate: eicosyltrimethylammonium chloride, and ditallowedimethylammonium chloride.

Materials that can be used to opacify compositions of the invention include fatty esters, opacifying polymers, such as styrene polymers, like OPACIFIER 653 from Morton, International, Inc.; and fatty alcohols. The following is a non-limiting list of fatty alcohols: cetyl alcohol; stearyl alcohol; cetearyl alcohol; behenyl alcohol; and arachidyl alcohol. Conditioning compositions of the invention which are not clear also can include Lexamine S-13, dicetylammonium chloride, and ceteareth-20.

Shampoo formulations are sometimes advantageous for treating scalp lesions such psoriasis of the scalp.

The hair shampoo composition of the present invention may contain nonionic surfactants or amphoteric surfactants in order to improve its cleansing performance.

Examples of the nonionic surfactant include, but are not limited to, polyoxyalkylene sorbitan fatty acid esters, polyoxyalkylene sorbitol fatty acid esters, polyoxyalkylene glycerin fatty acid esters, polyoxyalkylene fatty acid esters, polyoxyalkylene alkyl ethers, polyoxyalkylene alkylphenyl ethers, polyoxyalkylene (hydrogenated) castor oils, sucrose fatty acid esters, polyglycerin alkyl ethers, polyglycerin fatty acid esters, fatty acid alkanolamides, and alkyl glycosides. Of these, alkyl glycosides, polyoxyalkylene ($C_8$ to $C_{22}$) fatty acid esters, polyoxyethylene sorbitan fatty acid esters, polyoxyethylene hydrogenated castor oils and fatty acid alkanolamides are preferred. As the fatty acid alkanolamides, those with an acyl group having from 8 to 18, more preferably from 10 to 16 carbon atoms are preferred. As the fatty acid alkanolamides, either of monoalkanolamides or dialkanolamides may be used and those with a hydroxyalkyl group having 2 to 3 carbon atoms are preferred. Examples include oleic diethanolamide, palm kernel fatty acid diethanolamide, coconut oil fatty acid diethanolamide, lauric acid diethanolamide, polyoxyethylene coconut oil fatty acid monoethanolamide, coconut oil fatty acid monoethanolamide, lauric acid isopropanolamide and lauric acid monoethanolamide.

The amphoteric surfactants which can be used in the shampoo composition of the present invention include betaine surfactants such as alkyldimethylaminoacetic acid betaines and fatty acid amidopropylbetaines. As the fatty acid amidopropylbetaines, those with an acyl group having from 8 to 18, more preferably from 10 to 16 carbon atoms are preferred, with lauryl amidopropylbetaine, palm kernel amidopropylbetaine and cocamidopropylbetaine being especially preferred.

The nonionic surfactant and amphoteric surfactant may be incorporated in the hair shampoo composition of the present invention as needed. Two or more of them may be used in combination. When the hair shampoo composition of the present invention is provided in the form of an aqueous liquid shampoo, use of fatty acid amidopropylbetaine or fatty acid alkanolamide is preferred, because it not only improves foaming power but also provides the shampoo with adequate fluidity.

The content of the nonionic surfactant in the hair shampoo composition may fall within a range of from 0 to 15 wt. %, more preferably from 0.5 to 10 wt. %, still more preferably from 1 to 5 wt. % in the hair shampoo composition, while that of the amphoteric surfactant in the hair shampoo composition may fall within a range of from 0 to 10 wt. %, more preferably 0.5 to 8 wt. %, still more preferably from 1 to 5 wt. %.

The hair shampoo composition of the present invention may further contain a cationic polymer in consideration of the texture of foams, lubricated feeling of foams, reduction in the friction between hair strands upon shampooing and smoothness after drying. Examples of the cationic polymer include cationic cellulose derivatives, cationic starch, cationic guar gum derivatives, homopolymers of a diallyl quaternary ammonium salt, diallyl quaternary ammonium salt/acrylamide copolymers, quaternized polyvinylpyrrolidone derivatives, polyglycol-polyamine condensation products, vinylimidazolium trichloride/vinylpyrrolidone copolymers, hydroxyethyl cellulose/dimethyldiallyl ammonium chloride copolymers, vinylpyrrolidone/quaternized dimethylaminoethyl methacrylate copolymers, polyvinylpyrrolidone/alkylamino acrylate copolymers, polyvinylpyrrolidone/alkylaminoacrylate/vinyl caprolactam copolymers, vinylpyrrolidone/methacrylamidopropyl trimethylammonium chloride copolymers, alkylacrylamide/acrylate/alkylaminoalkyl acrylamide/polyethylene glycol methacrylate copolymers, adipic acid/dimethylaminohydroxypropylethylenetriamine copolymers (CALTALETINE manufactured by US Sandos Corp.), and cationic polymers described in Japanese Patent Laid-Open No. Sho 53-139734 and Japanese Patent Laid-Open No. Sho 60-36407. Of these, cationic cellulose derivatives and cationic guar gum derivatives are preferred.

Two or more of these cationic polymers may be used in combination. Its content in the hair shampoo composition of the present invention is preferably from 0.02 to 5 wt. %, more preferably from 0.05 to 1 wt. %, and even more preferably from 0.1 to 0.3 wt. % from the viewpoints of improvement in the foam quality upon shampooing, manageability of hair after drying and improvement in feel.

The hair shampoo composition of the present invention may further contain a conditioning component such as silicone in order to improve the finish after drying. Examples of the silicone include dimethylpolysiloxane, methylphenylpolysiloxane, amino-modified silicone, polyether-modified silicone, epoxy-modified silicone, fluorine-modified silicone, cyclic silicones, alkyl-modified silicones, and oxazoline-modified silicone. Of these, dimethylpolysiloxane, methylphenylpolysiloxane, amino-modified silicone polyether-modified silicone, oxazoline-modified silicone and cyclic silicones are preferred. Two or more of these silicones may be used in combination. Its (their) content preferably ranges from 0.01 to 20 wt. %, more preferably from 0.05 to 10 wt. %, still more preferably from 0.1 to 5 wt. % in the hair shampoo composition of the present invention.

The hair shampoo composition of the present invention may contain, in addition to the above-described components, water soluble polymers such as hydroxypropylmethyl cellulose, hydroxyl cellulose, polyvinyl alcohol, and polyethylene glycol; polyhydric alcohols such as sorbitol; humectants; chelating agents such as ethylene diamine tetraacetic acid (EDTA); drugs such as vitamin preparations; amino acids and derivatives thereof; fine particles of a polymer such as polyethylene, polystyrene, poly(methyl methacrylate), nylon or silicone, and hydrophobic products thereof; extracts derived from animals or plants; ultraviolet absorbers; pearling agents, antiseptics; bactericides; pH regulators; colorants; and fragrances, according to the using purpose.

The hair shampoo composition of the present invention may be provided in any form selected from liquid, powder, gel and granule as needed. A liquid composition using water or a lower alcohol as a solvent is preferred, with a liquid composition using water being especially preferred.

It is expected that during the life of this patent many relevant isothiocyanates will be identified and the scope of the term isothiocyanates is intended to include all such new technologies a priori.

As used herein the term "about" refers to +10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., Ed. (1994); "Culture of Animal Cells—A Manual of Basic Technique" by Freshney, Wiley-Liss, N.Y. (1994), Third Edition; "Current Protocols in Immunology" Volumes I-III Coligan J. E., Ed. (1994); Stites et al. (Eds.), "Basic and Clinical Immunology" (8th Edition), Appleton & Lange, Norwalk, Conn. (1994); Mishell and Shiigi (Eds.), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed. (1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Background

Isothiocyanates Exhibit an Antiproliferative Effect

Cruciferous are a source of isothiocyanates—Isothiocyanates are sulfur-containing compounds largely responsible for the typical flavor of cruciferous vegetables. Isothiocyanates are formed by the degradation of glucosinolates present in Cruciferous vegetables such as cabbage, broccoli and cauliflower. The degradation reaction of glucosinolates is catalyzed by a plant-specific myrosinase or the intestinal flora in the body. In the intact plant cell, glucosinolates are kept separate from the endogenous myrosinase which catalyzes their hydrolysis.

Isothiocyanates from Cruciferous plant extract inhibit cell proliferation—Prior art studies demonstrated that isothiocyanates isolated from seeds of cruciferous vegetables exhibit an inhibitory activity on K562 cells growth (Nastruzzi C et al., 2000, J. Agric. Food Chem. 48: 3572-5) and can stimulate apoptosis and confer protection against DNA damage in human colon cell lines (Bonnesen C et al., 2001, Cancer Res. 61: 6120-30). Isothiocyanate were isolated from various glucosinolates including sinigrin, gluconapin, progoitrin, epiprogoitrin, sinalbin, glucotropaeolin, glucoerucin, glucocheirolin and glucoraphenin and their inhibitory activity on the proliferation of K562 cells was determined (See Table 1 in Leoni, O, et al., 1997, Bioorganic and Medicinal Chemistry, 5: 1799-1806). The most potent isothiocyanates exhibited $IC_{50}$ values of <0.1 μM (for 2-Propenyl- and Benzyl-isothiocyanates) and 2.5 μM [for 4-(Methyl-thio)-butyl-isothiocyanate (MTBITC)] in inhibiting the growth of K562 cells [Leoni, 1997 (Supra)]. In addition, recent studies utilizing MTCITC demonstrated its specific effect on cell cycle arrest of leukemic cells at the G2/M transition (Fimognari C., et al., 2004, Investigational New Drugs 22: 119-129).

Example 1

Plant Seed Extract Containing 4-(Methylthio)Butylisthiocyanate is Capable of Treating Psoriasis Lesions A novel composition useful for treating psoriasis lesions was identified by the present inventor, as follows.

Materials and Experimental Methods

*Eruca Sativa* plant extract—An alcoholic extract made from the ripe seeds of rocket (*Eruca Sativa* Miller) plant (at a 1:1 ratio) was purchased from The Herbal Apothecary (Syston Leicester, England).

Preparation of an *Eruca Sativa* plant extract cream—The alcoholic plant extract of *E. Sativa* was mixed at a 15% final concentration with a base cream to form an emulsion (Base cream Batch No. 50402, C.T.R. Tel Aviv, Israel). The cream was water base to avoid the use of fatty acids which tend to relieve the dryness characterizing the psoriasis lesions.

Study subjects and application of cream—Psoriasis patients suffering from various degrees of psoriasis lesions participated in the study. Application of the *Eruca Sativa* plant extract cream was performed twice a day for four weeks on a single psoriasis lesion, while a second psoriasis lesion in the same individual was treated with the base cream devoid of the *Eruca Sativa* plant extract which was similarly applied twice a day for four weeks.

Experimental Results

Figure 3B:
Figure 3D:
Figure 3A:
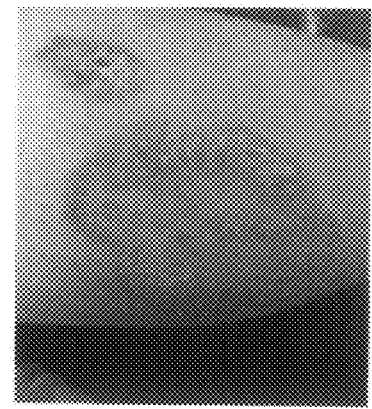
Figure 3C:

Treatment of moderate to severe psoriasis lesions using the *E. Sativa* cream—A 35 year-old woman who suffered from psoriasis since the age of 23 exhibited moderate to severe psoriasis lesions which cover 5% of her body surface. This patient was previously treated with various ointments and creams including daivonex (a vitamin D derivate) and steroids without any significant improvement. When enrolled to the study, the patient received the *E. Sativa* cream along with a placebo cream (i.e., the base cream devoid of the *E. Sativa* plant extract) and applied each cream on a single psoriasis lesion, twice a day, for four weeks. As is show in FIGS. 3a-d, a significant improvement was observed following treating the psoriasis lesion with the *E. Sativa* plant extract cream. In fact, the moderate to severe psoriasis lesion on the back of the leg (FIGS. 3a-b) was significantly reduced in size and almost completely disappeared following four weeks of treatment with the *E. Sativa* plant extract cream of the present invention (FIGS. 3c-d). On the other hand, the other psoriasis lesion which was treated with the placebo cream exhibited no improvements in size or degree of lesion (data not shown).

Treatment of light to moderate psoriasis lesions using the *E. Sativa* cream—Another 35 year-old woman who suffered from non-severe (light) to moderate degree of psoriasis lesions on her elbows (FIGS. 4a-b) exhibited a significant improvement of the lesion with a complete disappearance of the reddish thick eruptions following four weeks of treatment with the *E. Sativa* cream of the present invention (FIG. 4c).

Treatment of psoriasis in a diabetic patient—A 71 old woman who suffers for 10 years from moderate psoriasis lesions as well as from type II diabetes was treated with the *E. Sativa* cream on psoriasis lesions present on her elbows and with a placebo cream on psoriasis lesions present on her leg. During cream application, the psoriasis lesions of this patient were inspected every 3 days. After one week of treatment, a significant improvement in the elbow lesions treated with the *E. Sativa* cream of the present invention was observed. After 4 weeks of treatment (twice a day) the scaling of the lesion was significantly reduced and was close to normal and the silvery plaques were almost disappeared (compare FIGS. 5c-d with FIGS. 5a-b). These results are completely unexpected, especially in a diabetic patient in which the general healing process of all lesions is significantly slower than in non-diabetic patients.

Complete disappearance of light psoriasis lesions using the *E. Sativa* cream of the present invention—A psoriasis patient with light psoriasis lesions on the hands and elbows who was previously treated with hydrocortisone with salicyclic acid without any significant improvement, was treated with the *E. Sativa* cream of the present invention. Following three weeks of treatment (twice a day) the psoriasis lesions were completely disappeared (data not shown).

A significant relief in the degrees of pruritus and width of scaling following treatment with the *E. Sativa* cream of the present invention—A 45-year-old woman who suffered from psoriasis lesions on her legs was treated with the *E. Sativa* cream twice a day. A significant improvement in the degree of pruritus and width of scaling was reported following two months of treatment (data not shown).

The *E. Sativa* cream can relief rheumatoid arthritis-like psoriasis disease—A 67 year-old male who suffers from a severe rheumatoid arthritis-like psoriasis disease which covers more than 20% of its body surface was treated with various topical steroids and with the *E. Sativa* cream of the present invention. In this case, treatment with the cream resulted in only light relief of the psoriasis lesions.

Altogether, these results demonstrate that a topical use of the *E. Sativa* cream of the present invention can reduce scaling width, eliminate silvery plaques, and reduce the degree of pruritus of psoriasis lesions of various degrees. Thus, these results suggest the use of the *E. Sativa* cream of the present invention and/or other cruciferous plant extracts and/or isothiocyanates such as 2-Propenyl, 3-Butenyl, 2R-2-Hydroxy-3-butenyl-, 2S-2-Hydroxy-3-butenyl-, p-Hydroxybenzyl-, Benzyl, 4-Methyl-thio-butyl-, 3-Methyl-sulfonyl-propyl-, and/or 4-Methyl-sulfinyl-butenyl-isothiocyanates for the treatment of psoriasis.

Example 2

Enzymatic Preparation of
4-Methyl-Thio-Butyl-Isothiocyanate from
Glucoerucin Enriched Extract of *Eruca Sativa*

To efficiently treat psoriasis, the present inventor further isolated the 4-methyl-thio-butyl-isothiocyanate from an enriched fraction of glucoerucin extract prepared from the ripe seeds of rocket (*Eruca sativa*), as follows.

Materials and Experimental Methods

Extraction of glucoerucin from the ripe seeds of rocket (*Eruca sativa*)—To extract glucoerucin from the ripe seeds of rocket (*Eruca sativa*), 1 gram of seeds was heated for 24 hours at 100° C., homogenized for 5 minutes in 70% ethanol, following which the homogenate was heated for 30 minutes at 70° C., cooled down to room temperature and centrifuged for 15 minutes at 17000 g. The ethanol from the obtained supernatant was evaporated and after partial evaporation the remaining water fraction was filtered using 0.2/0.45 filter. The presence of glucoerucin was identified using HPLC (HP 1100) connected to UV/VIS detector (diod array) analysis (C18 column; Merck), using MeOH:$H_2O$ as eluents; and by LCMS (Micromass Quattro Ultima, England) following the methods of Bennett, 2004 (Supra).

Enzymatic formation of isothiocyanates (ITC)—To obtain 4-Methyl-thio-butyl-isothiocyanate (MTBITC) the glucoerucin was subjected to enzymatic hydrolysis with myrosinase (Sigma, Thioglucosidase EC. 3.2.3.1) in 0.1 M phosphate buffer, pH 7.0 (1 Unit/mg extract) essentially as described in Bennett, 2004 (Supra), followed by extraction in $CH_2Cl_2$ and evaporation of the solvent under vacuum using a Rotavapor [model No. RE121, Buchi (Switzerland)] attached to a water bath [model No. 461, Buchi (Switzerland)]. The resulting product was identified using GCMS (Varian) according to Bennett, 2004 (Supra). The purified glucoerucin hydrolysis products which contain MTBITC was stored under nitrogen at −20° C.

Experimental Results

Glucoerucin can be extracted from *Eruca sativa*—Glucoerucin was isolated from the seeds of *Eruca sativa* and the resulting product was characterized using HPLC (FIG. 6a), UV spectrum (FIG. 6b) and LCMS (FIG. 6c) analyses. As is shown in FIG. 6a, when the alcoholic extract of the *Eruca sativa* seeds was subjected to HPLC analysis, a sharp peak appeared after 8.5 minutes. The eluted material (at 8.5 minutes) was further subjected to UV spectrum analysis which (FIG. 6b). Further LCMS analysis revealed that the product eluted at 8.5 minutes from the HPLC exhibits an m/z (mass to charge ratio) of 420.57 (FIG. 6c) which corresponds to that of glucoerucin [See Bennett, 2004 (Supra)], demonstrating the presence of a glucoerucin-enriched extract.

4-methyl-thio-butyl-isothiocyanate can be obtained by enzymatically hydrolyzing glucoerucin using myrosinase—To enzymatically produce the isothiocyanate from glucoerucin, the glucoerucin extract was subjected to hydrolysis treatment using myrosinase and the products were further analyzed using HPLC. As is shown in FIGS. 7a-b, HPLC analyses performed prior to myrosinase treatment revealed a major peak at 8.5 minutes. After hydrolysis with myrosinase, the 8.5 minute peak disappeared and a new peak appeared at 2.5 minutes, as expected from the presence of myrosinase [See Bennett, 2004 (Supra)].

To further characterize the glucoerucin hydrolysis product, the ITC was extracted from the reaction mixture using dichloromethane, the solvent was then evaporated and the product was identified as MTBITC using GCMS analysis. As is shown in FIGS. 8a-b, a peak appeared at 12.92 minutes in gas chromatography (GS). The mass spectroscopy (MS) analysis revealed that the product eluted at 12.92 minutes from the GS exhibits a peak at m/z of 161, which corresponds to the molecular weight of 4-Methyl-thio-butyl-isothiocyanate (minus one hydrogen proton), and fragmentations in m/z of 115 (which corresponds to M-CH3-S) [See Bennett, 2004 (Supra)].

Altogether, these results demonstrate that glucoerucin can be extracted from the seeds of *eruca sativa* (rocket) and that in the presence of myrosinase, 4-Methyl-thio-butyl-isothiocyanate is formed. Based on the HPLC analysis the present inventor has estimated the level of glucoerucin in the extract to be about 70-80% w/w (glucoerucin/seed extract), all of which transforms into 4-Methyl-thio-butyl-isothiocyanate in the presence of myrosinase.

Example 3

Cytotoxicity Effects of 4-Methyl-Thio-Butyl-Isothiocyanate (MTBITC) on Hyperproliferative Cells The present inventor further determined the effect of the glucoerucin hydrolysis products which contain 4-methyl-thio-butyl-isothiocyanate on the proliferation of normal or hyperproliferative cells, as follow.

Materials and Experimental Methods—

Cell lines—The human keratinocyte cell line [HaCaT; (Boukamp et al 1988 The Journal of cell biology 106:761-771] are considered immortal, reveal a heteroploid stemline with specific stable marker chromosomes, but are not tumorigenic. They have a remarkable capacity for normal differentiation and thus offer a suitable and stable model for studying keratinocyte cells. The Jurkat T-leukemia cells are leukemia cells known to be affected in their cell-cycle progression and apoptosis induction by 4-(methylthio)butylisothiocyanate (Fimognari et al., 2004 Investigational New Drugs 22:119-129).

Cell culture conditions—HaCaT cells were cultured in Dulbecco's modification of Eagle's medium supplemented with 10% fetal bovine serum, 2% L-glutamine, and 1% antibiotic/antimycotic solution (Penicillin-Streptomycin Solution, Cat. No. 03-031-1B, Biological Industries Beth Haemek, Israel) under humidified atmosphere in the presence of 5% $CO_2$. The Jurkat T-leukemia cells were grown in suspension and propagated in RPMI 1640 supplemented with 10% heat-inactivated bovine serum, 1% antibiotics (Penicillin-Streptomycin Solution, Cat. No. 03-031-1B, Biological Industries, Israel). All cell culture materials were purchased from SIGMA and Biological Industries Beth Haemek, Israel.

In vitro antiproliferative assay—The effect of glucosinolate (e.g., glucoerucin in this case) hydrolysis products on cell proliferation was tested on two cell lines: the normal, non-cancerous HaCaT keratinocyte cell line and the Jurkat T leukemia cell line. Increasing concentrations of myrosinase-catalyzed hydrolysis products (which contain 4-Methyl-thio-butyl-isothiocyanate as shown in FIG. 8b and Example 2, hereinabove) from 0-25 µg/ml were added to the cell culture medium, following which the cells were seeded at a concentration of $5 \times 10^4$ cells per 1.5 cm tissue culture dish. For control, phosphate buffered saline (PBS) was added to the cell medium (10 µl per 1.5 cm tissue culture dish). The cells were cultured in the presence of the glucoerucin hydrolysis products for 4 days, during which aliquots of cell samples were subjected to cell proliferation assays using the XTT non-radioactive cytotoxicity assay kit (SIGMA) and FACS analysis (FACS Calibur, Becton Dickinson).

Experimental Results

Cytotoxicity effects of myrosinase-catalyzed hydrolysis product of glucoerucin—HaCaT and Jurkat T-leukemia cells were treated for 4 days with increasing concentrations (from 0-25 µg/ml) of glucoerucin hydrolysis products which contain 4-Methyl-thio-butyl-isothiocyanate. As is shown in FIG. 9, while treatment of HaCaT cells with 1.56-12.5 µg/ml of glucoerucin hydrolysis products had no significant effect on cell proliferation as compared to incubation in the presence of PBS, treatment of the HaCaT cells with 25 µg/ml resulted in a significant reduction of about 75% in cell viability. On the other hand, treatment of the Jurkat T-leukemia cells with 12.5 µg/ml resulted in a significant reduction (of about 40%) in cell viability (data not shown).

These results clearly demonstrate that the hydrolysis products of the purified glucoerucin of the present invention (i.e., MTBITC) are capable of inhibiting cell proliferation of hyperproliferative cells (such as the Jurkat T-leukemia cells) and are less cytotoxic to normal keratinocyte (e.g., HaCaT cells). The fact that the hyperproliferative cells are more susceptible to relatively low concentrations (e.g., 12.5 µg/ml) of the glucoerucin hydrolysis products suggests the beneficial effect of such hydrolysis products (e.g., MTBITC) on hyperproliferative keratinocytes and activated T cells found under psoriasis conditions (see for example, Jackson M, et al., 1999, FASEB J. 13: 495-502; Prinz J C, 2003, J. Eur. Acad. Dermatol. Venereol., 17: 257-70).

It should be noted that since the molecular weight of 4-Methyl-thio-butyl-isothiocyanate is 162 gram/mole and assuming that the glucoerucin extract of the present invention includes at least 70% glucoerucin (w/w), it is expected that a concentration of 10 µM 4-Methyl-thio-butyl-isothiocyanate is equivalent to about 2-3 µg/ml of glucoerucin hydrolysis product of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating a patient suffering from psoriasis comprising administering to the patient a therapeutically effective amount of a composition comprising a synthetic 4-Methyl-thio-butyl-isothicyanate, thereby treating the psoriasis in the patient.

2. The method of claim 1, wherein said composition further includes a carrier suitable for topical administration, injection, subcutaneous administration or intramuscle administration.

* * * * *